(12) United States Patent
Abribat et al.

(10) Patent No.: US 7,244,770 B2
(45) Date of Patent: Jul. 17, 2007

(54) METHOD FOR EVALUATING AN OPTIMAL DOSAGE OF DEFOAMERS IN A FERMENTATION PROCESS

(75) Inventors: Benoit Abribat, Saint Fargeau Ponthierry (FR); Jean-Pierre Molitor, Buthiers (FR); Christian De Haut, Boissise le Roi (FR); Stephanie Merlet, Boulogne (FR); Peter Claessens, Venray (NL)

(73) Assignee: Cognis France, S.A., Saint Martory (FR)

( * ) Notice: Subject to any disclaimer, the term of this patent is extended or adjusted under 35 U.S.C. 154(b) by 332 days.

(21) Appl. No.: 10/494,506

(22) PCT Filed: Oct. 26, 2002

(86) PCT No.: PCT/EP02/11982

§ 371 (c)(1),
(2), (4) Date: May 4, 2004

(87) PCT Pub. No.: WO03/040699

PCT Pub. Date: May 15, 2003

(65) Prior Publication Data

US 2005/0003508 A1    Jan. 6, 2005

(30) Foreign Application Priority Data

Nov. 5, 2001  (EP) .................................. 01402842

(51) Int. Cl.
*C21S 5/00* (2006.01)
*B01D 19/04* (2006.01)
*G01N 13/02* (2006.01)

(52) U.S. Cl. ..................... 516/115; 516/113; 516/904; 73/64.51; 137/170.1; 435/246; 435/812

(58) Field of Classification Search ................ 516/115; 137/170.1; 73/64.48, 64.51
See application file for complete search history.

(56) References Cited

U.S. PATENT DOCUMENTS

| | | | |
|---|---|---|---|
| 5,288,789 A | * | 2/1994 | McCarthy .................. 435/243 |
| 6,083,998 A | * | 7/2000 | Romualdo et al. .......... 516/117 |
| 2003/0078307 A1 | * | 4/2003 | Shinohara et al. .......... 516/113 |

FOREIGN PATENT DOCUMENTS

| | | |
|---|---|---|
| DE | 197 55 291 C1 | 5/1999 |
| DE | 19755291 C1 * | 5/1999 |
| EP | 0 389 157 A2 | 9/1990 |
| GB | 1 236 817 A | 6/1971 |
| JP | 09-126982 * | 5/1997 |
| JP | 09 126982 A | 5/1997 |

OTHER PUBLICATIONS

Matthes, Elger et al., Dynamic Surface Tension, Laboratory News, Apr. 2002, pp. 13-15.*

* cited by examiner

Primary Examiner—Randy Gulakowski
Assistant Examiner—Timothy J. Kugel
(74) Attorney, Agent, or Firm—John F. Daniels

(57) ABSTRACT

Methods suitable for selecting optimal defoamers for use in fermentation processes are described wherein the methods comprise: (a) determining an amount of each of two or more defoamers which provides a requisite dynamic surface tension of at most 50 mN/m at a particular frequency in a fermentation medium; and (b) selecting the defoamer which provides the requisite dynamic surface tension at the lowest amount. Methods for controlling foam by determining and adjusting dynamic surface tension are also described.

21 Claims, 1 Drawing Sheet

Figure 1:
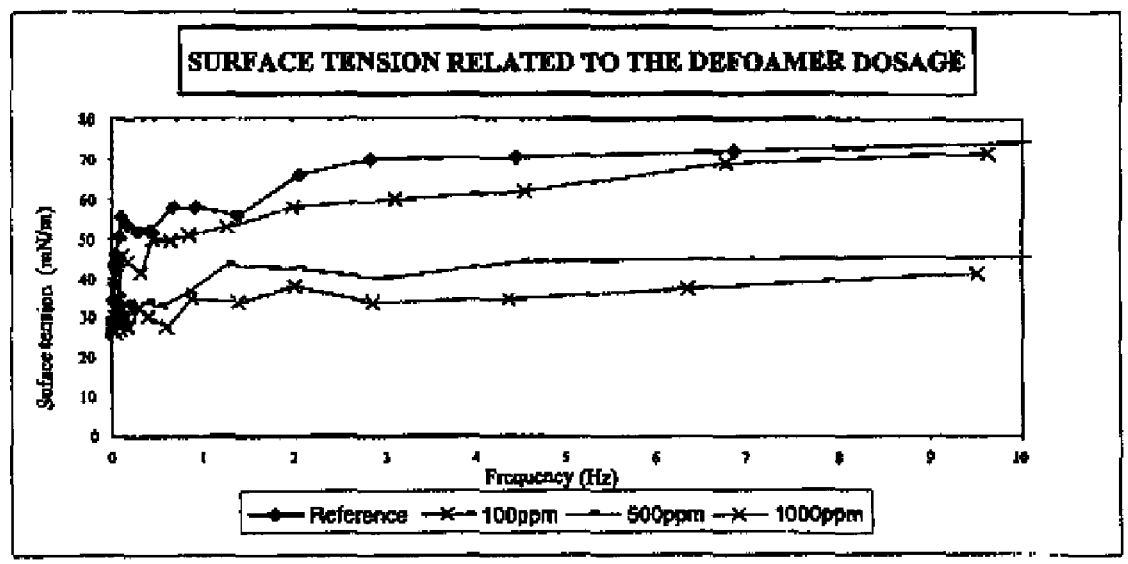

METHOD FOR EVALUATING AN OPTIMAL DOSAGE OF DEFOAMERS IN A FERMENTATION PROCESS

BACKGROUND OF THE INVENTION

The present invention relates to fermentation technology, in particular to the selection of appropriate defoamers and their efficient amounts, for such processes.

The screening and selection of defoamers for the use in fermentation processes is a complex, empirical and time-consuming process. However, in most fermentation processes, the adding of defoamers is critical to the overall yield, due to the fact, that strong foaming fermentation broth is difficult to control and often obliges to lower the filling of the fermenter, hence the overall productivity of each fermentation cycle and batch. Large additions of non appropriated defoamers can also lead to severe troubles in downstream operations like ultrafiltration, microfiltration or ion-exchange processes. Foam is a colloid system of gas dispersed into a liquid. Aeration occurs when dispersed small bubbles are formed in the liquid and remain trapped without coalescing. For the foam formation and stabilisation, a surface-active element is added which is able to form an elastic layer at the surface. Foam is formed when 1) a bubble of gas (in particular air) is developed in a liquid (in particular water) and is immediately coated with the surfactant, 2) the bubble rises to the surface and forms there an elastic skin of surfactant molecules and water, 3) the bubble is stable enough to remain at the surface without breaking. Foam is stabilised by the combined Maragoni and Gibbs effects. They define the surface tension modification, which creates this elastic more or less thick bubble wall. The use of defoamers permits the control of the foam thanks to their specific properties of reducing the surface tension of the bubble, preventing the water and foaming surfactant from entering the bubble, improving their drainage from the bubble and improving the de-aeration.

In most of the fermentation processes, the process requires a strong dispersion of micro-bubbles of air into the media, in order to permit the oxygen transfer from the bubbles towards the micro-organisms. Foam in the fermenter is created, with this high level of aeration, by all components that are present one after the other or together during the process: Nutrients, Biomass, Product, added surfactant, residues etc. Each of these compounds generates a type of foam, which can be different from the other and that cumulate their foaming power. For the best performances, the defoamer should be versatile enough in order to be adapted to each type of foaming components. The performances of the defoamers are characterised in two main properties, the knock-down effect and the hold-out effect. The knock-down effect is the ability of the product to quickly destroy existing foam, whereby the hold-out effect relates to the ability of the product to prevent the foam formation for a long time.

In the past, the selection of appropriate defoamers requires a complete series of laboratory fermentation trials, which are expensive and time consuming. Furthermore, most of the time, the results obtained from the laboratory tests are poorly correlated to the industrial trials.

It is therefore a standing demand in the fermentation industry to develop new test methods which reduce both time and costs for selecting appropriate defoamers for a fermentation processes.

BRIEF SUMMARY OF THE INVENTION

The present invention relates, in general, to fermentation technology, in particular to the selection of appropriate defoamers and their efficient amounts, for such processes.

Many chemical and physical processes which use surfactants are completed in fractions of second. For dynamic processes, surface tension can change dramatically over a time scale measured in terms of milliseconds. It was found that the measurement of a certain physical property of an aqueous fermentation media could be used for a quicker screening of defoamers.

In a first embodiment, a method for selecting an optimal dosage of defoamers for aqueous fermentation processes, comprising as a first step the measurement of the dynamic surface tension of a defoamer compound and, as a second step, determining the amount of the defoamer compound in the fermentation media which gives a surface tension of at maximum 50 mN/m at 10 Hz, and then selecting the defoamer compound, which gives the required dynamic surface tension at the lowest amount of the compound.

DETAILED DESCRIPTION OF THE INVENTION

All fermentation media contain some surface-active compounds which reduce the static surface tension of the liquid from approx. 73 mN/m to approx. 40-50 mN/m or even approx. 35 mN/m, when the concerned media contains as well chemical surfactants. Experimentally it has been determined that a defoamer should decrease the foaming media surface tension of some 5 to 10 mN/m. Nevertheless, this property is not sufficient for a defoamer selection in fermentation, as industrially the media is under high agitation and aeration conditions. Therefore, a dynamic surface tension method is required. This means, that the surface tension under agitation is measured. A traditional ring or plate tensiometer can not measure the fast changes. However, the bubble pressure technique can do so reproducibly.

The method of the invention preferably makes use of a SITA-online t60 dynamic tensiometer, which provides the surface tension of a liquid by measuring the pressure of a bubble of air, when it is formed in a liquid. This is done by pumping the air through a capillary with radius r into the liquid to be analysed. According to Young-Laplace, the difference of pressure "delta p" which is needed to form bubbles is proportional to the surface tension sigma, as given in the following equation:

$$\text{sigma} = \text{delta } p \times r/2$$

The bubbles are injected at a frequency varying from zero, static surface tension, up to 60 Hz, which is representative of the dynamic surface tension. The tensiometer directly provides the surface tension value.

In particular, 100 ml of a fermentation media at the process temperature, which is in the range of 25 to 40, especially 30 to 37° C., is prepared in a magnetic stirred bucket. The tensiometer capillary is introduced in this media and the experiments commence with automatic record of the surface tension as the frequency raises from 0.008 to 10 Hz. This evaluation was made with a reference containing no defoamer and compared with a medium containing the tested defoamers.

In FIG. 1, the results of a test of a certain defoamer series adapted to the fermentation industry was tested at three different amounts (100, 500 and 1000 ppm). The surface tension of the reference varies from approx. 30 mN/m at 0.008 Hz to approx. 60 mN/m at 1 Hz and then steadily up to about 65 mN/m at 10 Hz. With a defoamer, the behaviour of the surface tension is similar, but with somewhat lower values; the higher the dosage of the defoamer is, the lower the surface tension values are.

According to the present invention, it was found at 50 mN/m is the appropriate dynamic surface tension for a defoamer in aqueous fermentation media. To select the appropriate defoamer compound for a certain fermentation process, it is only necessary to determine the compound which gives the desired dynamic surface tension at the lowest amounts of the tested compounds.

The method according to the invention can be used for a broad variety of defoamer compounds, commonly used in industry. Traditionally, antifoaming agents were often single-component liquid systems or homogeneous solutions derived from vegetable oils or their constituent glyceride oils and fatty acids. Other useful materials included mineral oils and their derivatives. However, more complex formulations were also known, including aqueous sols derived from plant phosphatides, as well as other water-soluble or water-emulsifiable preparations. Modern antifoaming agents (also called defoamers) are formulated to meet more diverse demands, including optimal effectiveness, easy application in an industrial context, convenient dosage, low volatility, and safety from both toxicological and ecological standpoints. Most defoamers are composites rather than simple substances. Several groups can be distinguished:

1) Liquid single-component systems or homogeneous solutions

2) Dispersions of hydrophobic solids in a carrier oil

3) Aqueous or water-containing emulsions or suspensions

4) Solid defoamer formulations

The functional components of a foam inhibitor can be divided into four categories:

1) Carrier oils

2) Active ingredients

3) Amphiphilic substances

4) Coupling and stabilising agents.

Foam-inhibiting emulsions contain water, which serves as the continuous phase. Solid foam inhibitors are free-flowing powders in which the foam-inhibiting ingredients, as well as any emulsifying or dispersing agents, are bound adsorptively to an inorganic sorbent such as calcium silicate or sodium triphosphate, or to a polymeric organic matrix such as methyl cellulose. Particulate solid antifoaming ingredients suitable for incorporation into detergent powder compositions comprise a core that consists of an oily, solid, or gel-like carrier material. The core supports the antifoaming substances and is surrounded by a coating which is disrupted on contact with water to release the antifoaming substances.

In accordance with the present invention, hydrophobic fats and waxes include the following materials, which are preferred defoamers:
1. Polyoxyalkylene derived from ethylene oxide, propylene oxide and butylene oxide;
2. Polyoxyalkylene based on glycerol, polyglycerine, trimethylolpropane, sorbitol and sugar derivatives;
3. Fatty acid esters of monofunctional and polyfunctional alcohols and polyoxyalkylenes;
4. Fatty acid amides and sulfonamides;
5. Paraffinic hydrocarbon waxes, ozokerite, and montan wax;
6. Phosphoric acid mono-, di-, and triesters of short- and long-chain fatty alcohols;
7. Short- and long-chain natural or synthetic fatty alcohols;
8. Water-insoluble soaps of long-chain fatty acids, including aluminum stearate, calcium stearate, and calcium behenate;
9. Silicone derivatives and alkoxylated; and
10. Perfluorinated fatty alcohols.

Most preferred are defoamers of the Clerol®-type (Cognis), containing fatty alkylpolyglycolesters. Furthermore, the method is not critical as to the temperature or pH of the media. As far as the same properties are used for the evaluation and the industrial process, the selection according to the invention will obtain the most efficient defoamer compound. Due to the different contributions to the foaming capacity of the various compounds in the fermentation broth, it is necessary to evaluate the defoamer with precisely the composition, which will be used later in the industrial stage.

The claimed methods allow to determine quickly and cost-efficiently the appropriate, most efficient defoamer for a certain fermentation process.

A second embodiment of the present invention concerns a method to control foam in aqueous fermentation processes, whereby in a first step, the surface tension of the aqueous fermentation broth is measured in regular time intervals, and, in the case that the surface tension reaches or exceeds 50 mN/m at 10 Hz, in a second step an amount of defoamer is added to the fermentation broth until the surface tension is below 50 mN/m at 10 Hz and steps one and two are repeated until the end of the fermentation process. This method could be obtained by known technical means, preferred by using a SITA-online t60 dynamic tensiometer for the measurement of the surface tension. However, it is well within the scope of the present invention to use tensiometers for an online control of foam generation in industrial aqueous fermentation processes.

EXAMPLES

In a 5-liter fermenter, containing a protein medium, stirred at 450 rpm at 30° C., various defoamer compounds were examined. In the following table, the compounds are listed together with their dosage, necessary to obtain a surface tension of at maximum 50 mN/m at 10 Hz (column 2), and the minimum defoamer dosage, necessary to control the foam in the fermenter (column 3, laboratory defoamer tests). The latter amount was determined by standard methods.

TABLE 1

| | Foaming media, protein juice | |
|---|---|---|
| Defoamer | Minimum defoamer dosage (ppm) in order to obtain a surface tension of at maximum 50 mN/m at 10 Hz | Minimum defoamer dosage (ppm) necessary to control the foam in the fermenter |
| Rapeseed methy ester | 26000 | 200 |
| Clerol FBA 3107 | 850 | 38 |
| Clerol FBA 975 | 750 | 38 |
| Clerol FBA 5057 | 700 | 38 |
| Clerol LQ 217 | 700 | 38 |
| Foamaster EEA 142 | 700 | 38 |
| Clerol DT 5078 | 600 | 38 |
| Clerol FBA 847 | 600 | 25 |
| Clerol FBA 3003 | 600 | 25 |
| Clerol EBA 265 | 400 | 25 |

TABLE 1-continued

Foaming media, protein juice

| Defoamer | Minimum defoamer dosage (ppm) in order to obtain a surface tension of at maximum 50 mN/m at 10 Hz | Minimum defoamer dosage (ppm) necessary to control the foam in the fermenter |
|---|---|---|
| Clerol FBA 515 B | 400 | 25 |
| Clerol LQ 2012 | 300 | 13 |

From the above results, a good correlation between defoamer performance and lowering of the surface tension could be observed. In the present example, Clerol® LQ 2012 would be the most efficient defoamer compound according to the method of the present invention.

TABLE 2

Foaming media, molasses

| Defoamer | Minimum defoamer dosage (ppm) in order to obtain a surface tension of of at maximum 50 mN/m at 10 Hz | Minimum defoamer dosage (ppm) necessary to control the foam in the fermenter |
|---|---|---|
| Clerol FDG 5066 | >2000 ppm | 375 ppm |
| Clerol FBA 5059 | 1200 ppm | 200 ppm |
| Clerol FBA 975 | >1200 ppm | 175 ppm |
| Clerol FBA 3107 | >1200 ppm | 150 ppm |
| Clerol FBA 3003 | 1000 ppm | 125 ppm |
| Clerol FBA 5078 | 1000 ppm | 125 ppm |
| Dehysan Z 2226 | 500 ppm | 150 ppm |
| Clerol FBA 515 B | 500 ppm | 75 ppm |
| Clerol FBA 5057 | 500 ppm | 75 ppm |
| Clerol LQ 2012 | 500 ppm | 50 ppm |
| Clerol FBA 847 | 300 ppm | 25 ppm |

Again, a good correlation between defoamer performance and lowering of the surface tension could be observed. In the present example, Clerol® FBA 847 would be the most efficient defoamer compound according to the method of the present invention.

The invention claimed is:

1. A method comprising:
   (a) determining an amount of each of two or more defoamers which provides a requisite dynamic surface tension of at most 50 mN/m at a particular frequency in a fermentation medium; and
   (b) selecting the defoamer which provides the requisite dynamic surface tension at the lowest amount.

2. The method according to claim 1, wherein the particular frequency is from 0.008 to 10 Hz.

3. The method according to claim 2, wherein the fermentation medium is aqueous.

4. The method according to claim 3, wherein the requisite dynamic surface tension is determined by measurement with a dynamic tensiometer.

5. The method according to claim 1, wherein the fermentation medium is aqueous.

6. The method according to claim 5, wherein the requisite dynamic surface tension is determined by measurement with a dynamic tensiometer.

7. The method according to claim 1, wherein the amount of each of the two or more defoamers which provides the requisite dynamic surface tension is determined at separate times.

8. The method according to claim 1, wherein the amount of each of the two or more defoamers which provides the requisite dynamic surface tension is determined contemporaneously.

9. The method according to claim 1, wherein the particular frequency is from greater than zero to 60 Hz.

10. The method according to claim 1, wherein the particular frequency is 10 Hz.

11. The method according to claim 1, wherein the fermentation medium comprises an aqueous protein composition.

12. The method according to claim 1, wherein the requisite dynamic surface tension is determined by measuring the pressure of a bubble of air formed in the fermentation medium.

13. The method according to claim 1, wherein the requisite dynamic surface tension is determined by measurement with a dynamic tensiometer.

14. The method according to claim 1 wherein the selected defoamer of (b) comprises a fatty alkylpolyglycol ester.

15. A method comprising:
   (a) determining an amount of each of two or more defoamers which provides a requisite dynamic surface tension of at most 50 mN/m at 10 Hz in an aqueous fermentation medium by measurement with a dynamic tensiometer;
   (b) selecting the defoamer which provides the requisite dynamic surface tension at the lowest amount.

16. The method according to claim 15 wherein the selected defoamer of (b) comprises a fatty alkylpolyglycol ester.

17. A method for controlling foam in a fermentation process, said method comprising:
   (a) providing a fermentation broth;
   (b) determining the dynamic surface tension of the fermentation broth during fermentation; and
   (c) if the dynamic surface tension of the fermentation broth equals or exceeds 50 mN/m at 10 Hz, adding an amount of defoamer sufficient to reduce the dynamic surface tension to below 50 mN/m at 10 Hz.

18. The method according to claim 17, wherein the method further comprises repeating the determination of dynamic surface tension and the addition of defoamer, when dynamic surface tension of the fermentation broth equals or exceeds 50 mN/m at 10 Hz, at regular time intervals one or more times during the fermentation.

19. The method according to claim 18, wherein the dynamic surface tension is determined by measurement with a dynamic tensiometer.

20. The method according to claim 17, wherein the dynamic surface tension is determined by measurement with a dynamic tensiometer.

21. The method according to claim 17 wherein the defoamer comprises a fatty alkylpolyglycol ester.

* * * * *